United States Patent [19]
Cosmescu

[11] Patent Number: 5,114,422
[45] Date of Patent: May 19, 1992

[54] LASER LAPAROSCOPE ASSEMBLY AND METHOD THEREFOR

[76] Inventor: Ioan Cosmescu, 14449 N. 22nd St., Phoenix, Ariz. 85022

[21] Appl. No.: 448,329

[22] Filed: Dec. 11, 1989

[51] Int. Cl.⁵ .............................................. A61B 17/36
[52] U.S. Cl. .......................................... 606/14; 385/39
[58] Field of Search ................... 128/395, 398; 606/13, 606/14, 15, 16, 17, 18, 19; 350/96.18, 96.2

[56] References Cited

U.S. PATENT DOCUMENTS

| | | | |
|---|---|---|---|
| 3,865,113 | 2/1975 | Sharon | 600/19 |
| 4,451,115 | 5/1984 | Nicia | 350/96.18 |
| 4,526,170 | 7/1985 | Tanner | 606/16 |
| 4,532,400 | 7/1985 | Toida | 606/16 |
| 4,542,956 | 9/1985 | McCrickerd | 350/96.2 |
| 4,658,817 | 4/1987 | Hardy | 128/395 |
| 4,886,337 | 12/1989 | Raagaard | 350/96.2 |
| 4,895,145 | 1/1990 | Joffe | 606/11 |

FOREIGN PATENT DOCUMENTS 2488699 2/1982 France .................... 350/96.2

*Primary Examiner*—Kyle L. Howell
*Assistant Examiner*—Robert S. Nasser, Jr.
*Attorney, Agent, or Firm*—Harry M. Weiss

[57] ABSTRACT

A laser laparoscope assembly and method therefor are provided. The assembly includes a laser, a laparoscope, and an adjustable coupler. The adjustable coupler is used for interconnecting the laser to the laparoscope, or tissue treating instrument. The adjustable coupler has adjustably offset screws for adjustment normal to a laser beam axis and has adjustable tilt screws for tilting a laparoscope passage in order to align a laparoscope passage axis with the laser beam axis whereby a beam contact point and a reflected beam within the laparoscope is avoided.

4 Claims, 4 Drawing Sheets

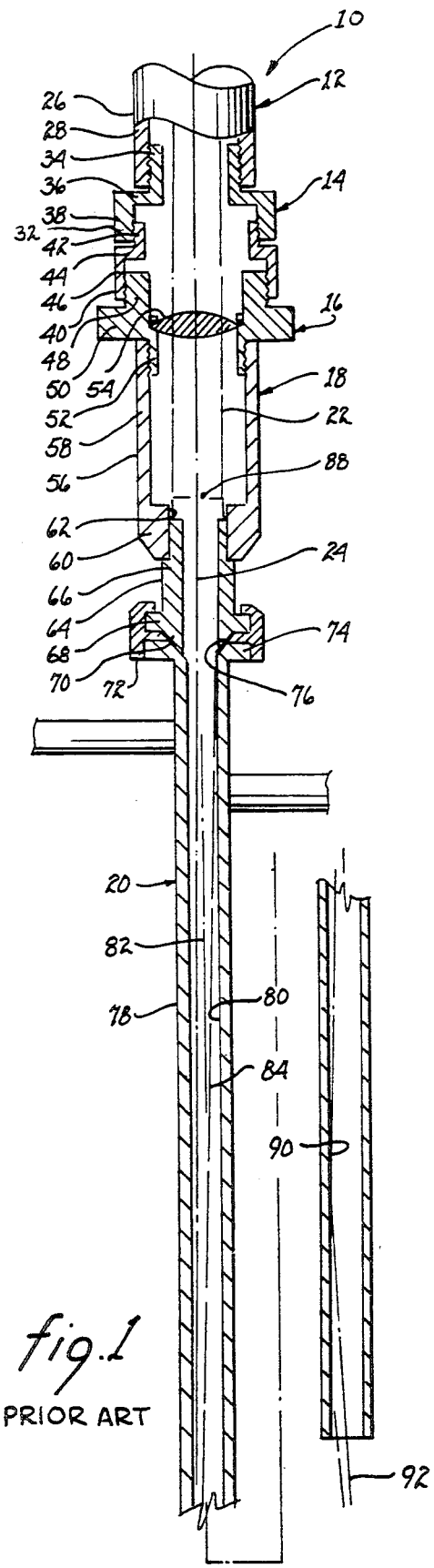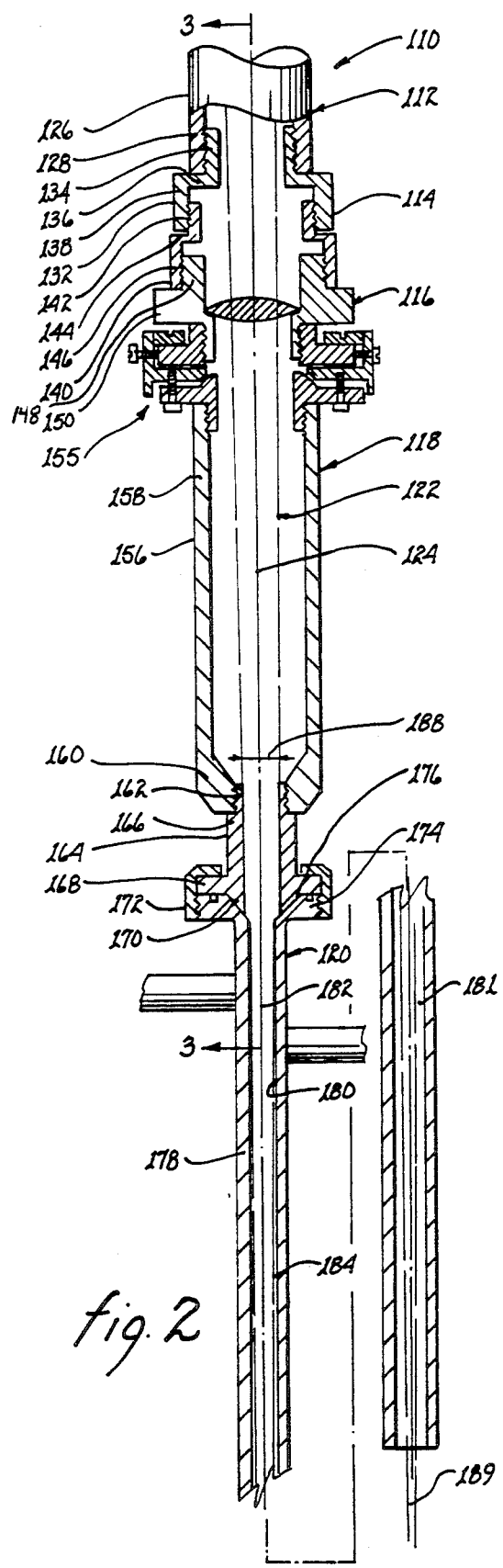
fig.1 PRIOR ART
fig.2

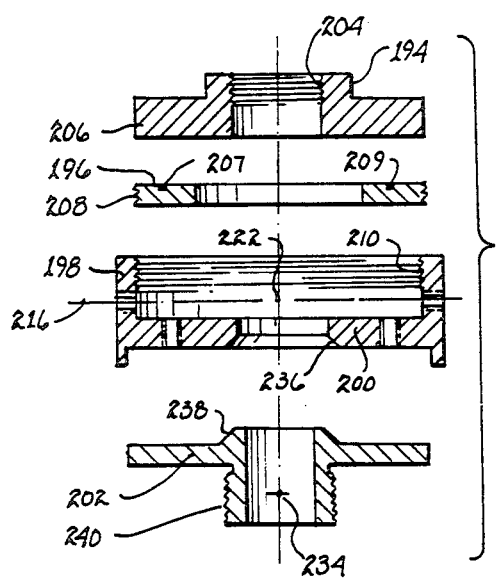
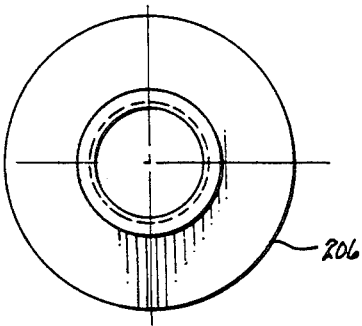
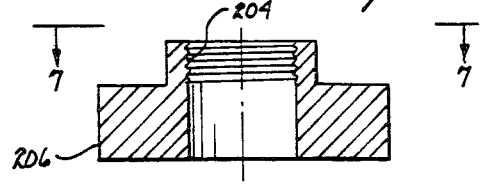
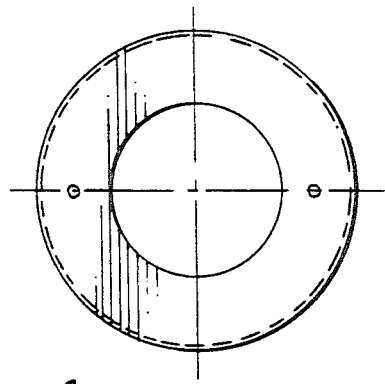
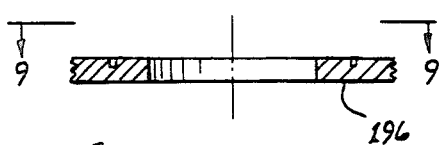
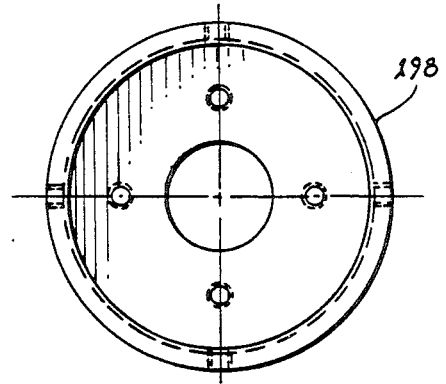
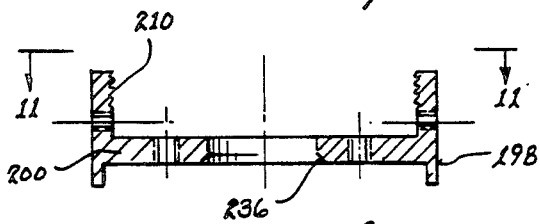

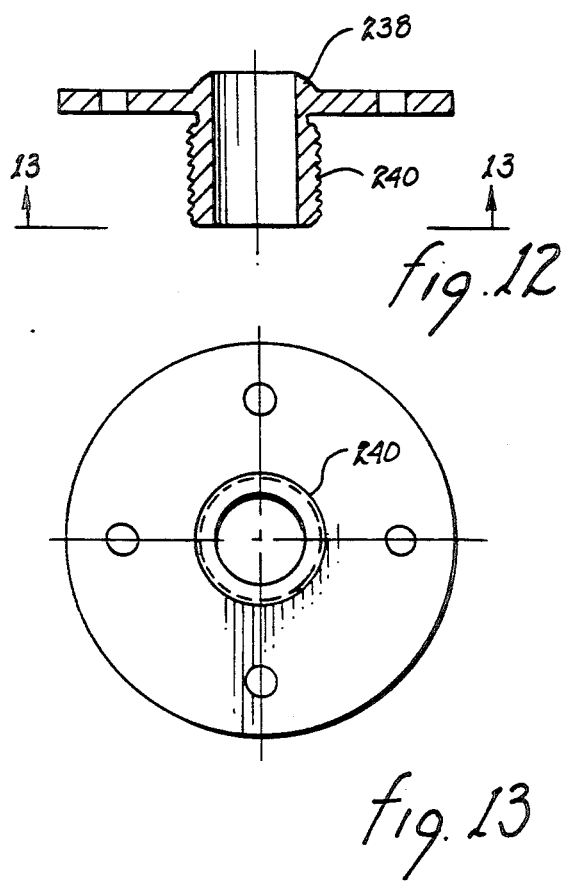
fig. 12
fig. 13
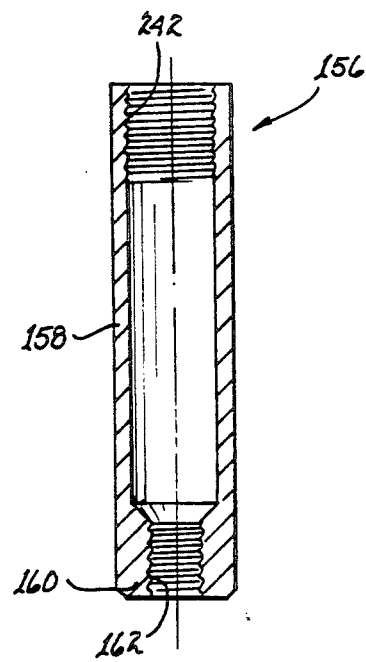
fig. 14
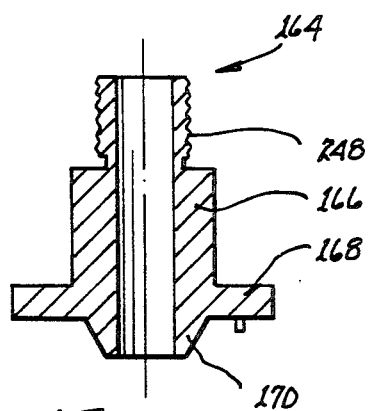
fig. 15
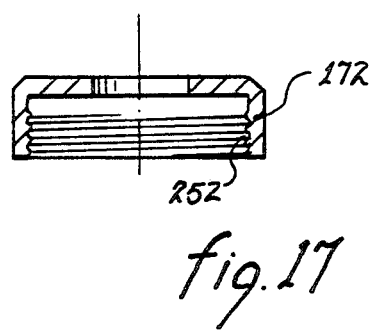
fig. 17
fig. 16

LASER LAPAROSCOPE ASSEMBLY AND METHOD THEREFOR

The invention relates to a laser laparoscope assembly and method therefor, and in particular the invention relates to a laser laparoscope assembly and method therefor having an adjustable coupler unit for coupling a laser to a laparoscope and for aligning a laparoscope passage axis with a laser beam axis.

BACKGROUND OF THE INVENTION

The prior art laser laparoscope assembly includes a laser having a laser beam passage with a passage axis, a laparoscope having a laser beam passage with a passage axis, and a coupler unit for connecting the laser to the laparoscope and for aligning the laparoscope passage axis with the laser passage axis.

One problem with the prior art laser laparoscope assembly is that a relatively slight offset, or a relatively slight tilt, of the laser beam in the laser beam passage causes a contact point and a consequent reflected laser beam within the laparoscope passage. Such offset, or tilt, of the laser beam in the laser beam passage can be caused within the laser by, for example, a mirror misalignment, or a like cause.

SUMMARY OF THIS INVENTION

According to the present invention, a laser laparoscope assembly is provided which will achieve a fixed, permanent alignment. This assembly includes a laser having a laser beam passage for a laser beam with a laser beam axis, a laparoscope having a laparoscope passage with a passage axis, and an adjustable coupler for connecting the laser to the laparoscope and for aligning the laparoscope passage axis with the laser beam axis. The adjustable coupler is comprised of a first portion fixedly connected to the laser, and a second and third portion fixedly connected to the laparoscope. The second portion having an adjustable offset means for slightly offsetting the second portion relative to the first portion in a direction normal to the laser beam axis. The third portion having an adjustable tilt means for slightly tilting the laparoscope passage axis.

By using the offset means and the tilt means, the laparoscope passage axis can be substantially aligned with the laser beam axis, thereby avoiding a contact point and consequent reflected laser beam within the laparoscope passage.

The foregoing and other objects, features and advantages will be apparent from the following description of the preferred embodiment of the invention as illustrated in the accompanying drawings.

BRIEF DESCRIPTION OF THE DRAWINGS

FIG. 1 is a cutaway elevation view of a prior art laser laparoscope;

FIG. 2 is a cutaway elevation view of a laser laparoscope according to the subject invention;

FIG. 5 is an enlarged view of a disassembled portion of FIG. 4;

FIG. 6 is an enlarged detail view of a portion of FIG. 4;

FIG. 7 is a plane view as taken along the line 7—7 of FIG. 6;

FIG. 8 is an enlarged detail view of another portion of FIG. 4;

FIG. 9 is a plane as taken along the line 9—9 of FIG. 8;

FIG. 10 is an enlarged detail view of another portion of FIG. 4;

FIG. 11 is a plane view as taken along the line 11—11 of FIG. 10;

FIG. 12 is an enlarged detail view of another portion of FIG. 4;

FIG. 13 is a section view as taken along the line 13—13 of FIG. 12;

FIG. 14 is an enlarged detail view of another portion of FIG. 4;

FIG. 15 is an enlarged detail view of another portion of FIG. 4;

FIG. 16 is an enlarged view of a portion of FIG. 15; and

FIG. 17 is an enlarged detail view of another portion of FIG. 4.

DESCRIPTION OF THE PREFERRED EMBODIMENT

Figure 3:
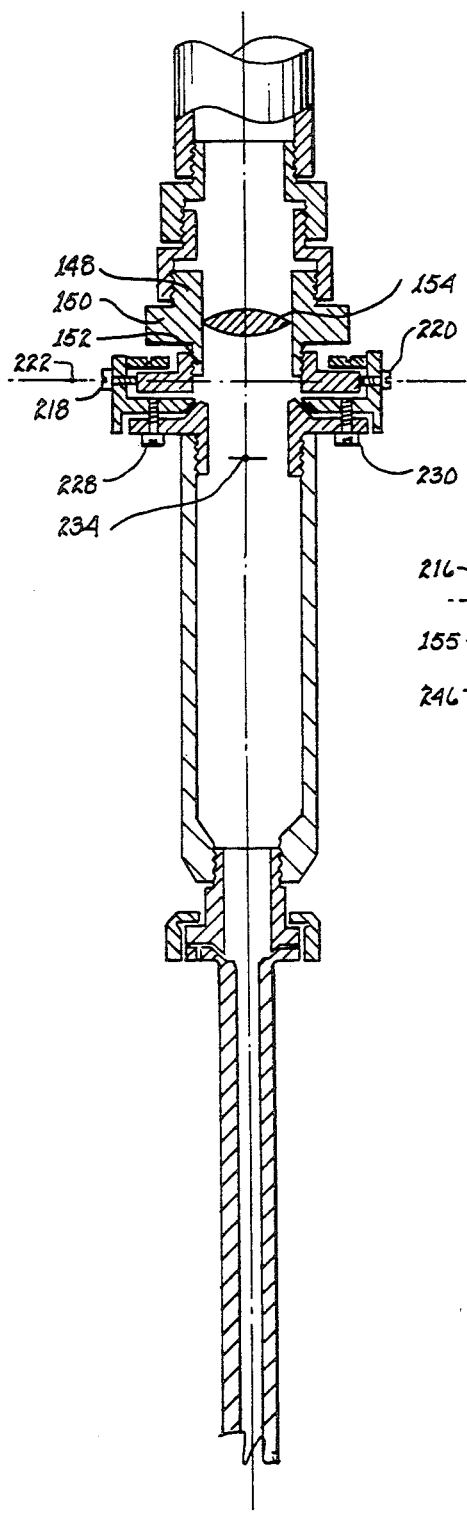
FIG. 3 is a sectional view as taken along the line 3—3 of FIG. 2.

As shown in FIG. 1, a prior art laser laparoscope assembly 10 is provided. Prior art assembly 10 includes a laser 12, an adaptor 14, a lens unit 16, a coupler 18, and a laparoscope or instrument 20.

The prior art laser 12 has a laser beam 22 with a laser beam axis 24. The laser 12 has an arm 26 which has a cylindrical wall 28.

The prior art adaptor 14 has a first adaptor portion 32, which has an upper wall 34, a web wall 36, and a lower wall 38. The adaptor 14 has a second adaptor portion 40, which has an upper wall 42, a web wall 44, and a lower wall 46.

The prior art lens unit 16 has an upper wall 48, a web wall 50, a lower wall 52, and a lens 54.

The prior art coupler 18, which is a fixed coupler, has a coupler cylinder 56, which has an upper wall 58, and a lower wall 60 with an inner surface 62. The coupler 18 also has an end coupler portion 64, which has an upper wall 66, a lower flanged wall 68, a projecting conical wall 70, and a separate ring member 72 mounted on the flanged wall 68.

The prior art laparoscope 20 has a flanged upper portion 74 which has a conical recess 76 that receives the wall 70. The laparoscope 20 has an elongate cylindrical wall 78, which has an inner surface 80. The laparoscope 20 also has an elongate axis 82, which is not aligned with the laser beam axis 24. The laparoscope 20 is a tissue treating instrument.

The prior art laser beam 22 has a tapered outer surface 84, and has an upper outside diameter 86 at the lens 54. The laser beam 22 also has a lower outside diameter 88 adjacent to an upper end of the surface 62. In the prior art embodiment, the upper diameter 86 is about 8 millimeters, and the lower diameter 88 is about 7 millimeters. The beam 22 has a contact point or area 90 which causes a reflected beam 92. One problem with the assembly 10 is the presence of the contact point 90 and reflected beam 92. Another problem with the assembly 10 is the loss of beam power due to an interference, created in the vicinity of the flanged portion 74, as the laser beam 22 having a diameter of about 6 millimeters enters the cylindrical wall 78 having an inside diameter of about 4 millimeters.

As shown in FIGS. 2 through 17, a laser laparoscope assembly 110 according to the subject invention is provided. The assembly 110 includes a laser 112, an adaptor 114, a lens unit 116, an adjustable coupler 118, and a laparoscope 120.

The laser 112 has a laser beam 122, which has a laser beam axis 124. Laser 112 also has an arm 126, which has a cylindrical wall 128.

The adaptor 114 has a first adaptor portion 132, which has an upper wall 134, a web wall 136, and a lower wall 138. The adaptor 114 also has a second adaptor portion 140, which has an upper wall 142, a web wall 144, and a lower wall 146.

The lens unit 116 has an upper wall 148, a web wall 150, a lower wall 152, and a lens.

The adjustable coupler 118 has an adjustable unit 155. The coupler 118 also has a coupler cylinder 156, which has an upper wall 158, and a lower wall 160 with an inner surface 162. The coupler 118 also has an end coupler portion 164, which has an upper wall 166, a lower flanged wall 168, a projecting conical wall 170, and a ring member 172 mounted on flanged wall 168. The cylinder 156 is about twice as long as the prior art cylinder 56.

The laparoscope 120 has a flanged upper portion 176, which has a conical recess 176, for receiving the wall 170. The laparoscope 120 has an elongate wall 178, which has an inner surface 180, that forms an elongate cylindrical passage 181, with a passage axis 182.

The laser beam 122 has a tapered outer surface 184, and has an upper, outside diameter 186 at the lens 154. The laser beam 122 also has a lower, outside diameter 188 at the upper end of the wall surface 162. The upper diameter 186 is about 8 millimeters. The laser beam 122 has a focused laser beam portion 189 at its bottom end. There is substantially, no power loss due to an interference, when the laser beam 122 enters the laparoscope 120 because the laser beam 122 has about a 4 millimeter diameter and the laparoscope passage surface 180 also has about a 4 millimeter inside diameter.

Figure 4:
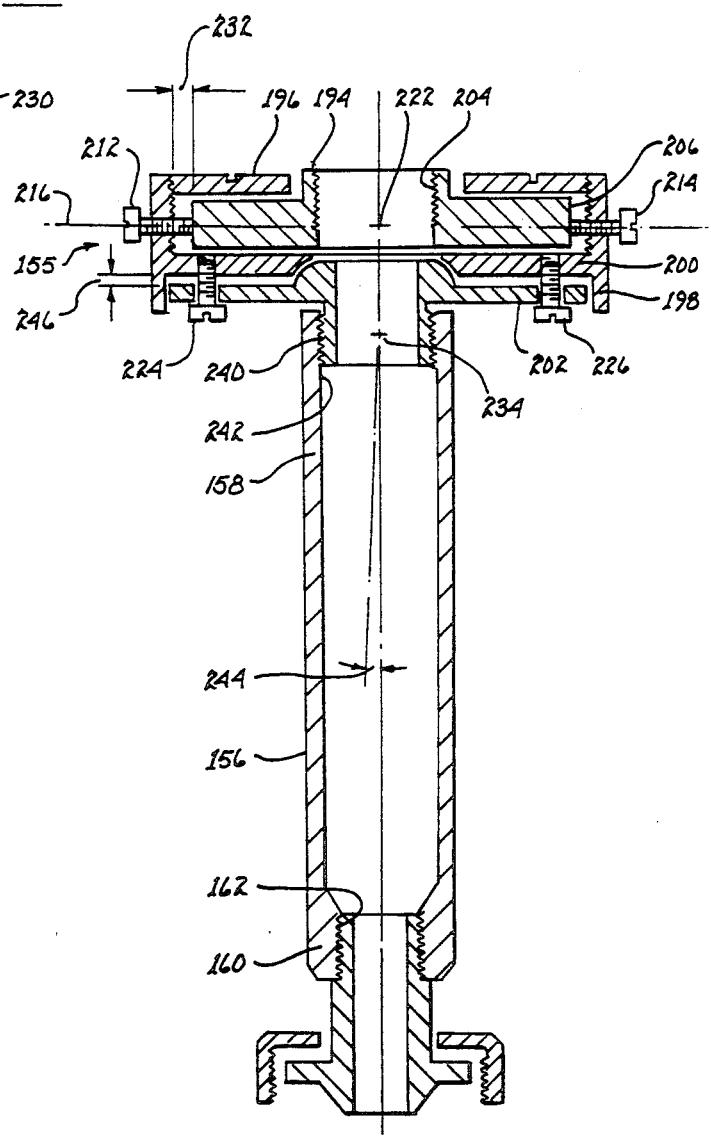
FIG. 4 is an enlarged sectional view of the adjustable coupler unit shown in FIG. 3 as taken through lines 4—4 of FIG. 3.

As shown in FIGS. 3 and 4, the adjusting unit 155 has a flange plate 194 which is fixedly connected to the lower wall 152, and has a lock plate 196 for holding flange plate 194. The adjusting unit 155 also has a cylindrical plate 198, which has an inner web plate 200, and has a tilt plate 202, which is fixedly connected to the coupler cylinder 156.

The flange plate 194 has an inner threaded surface 204 for attachment to the lower wall 152, and has an outer bearing surface 206.

As shown in FIG. 5, the lock plate 196 has an outer threaded surface 208 for engaging the cylindrical plate 198. The lock plate 196, also has two lock key holes 207, 209.

The cylindrical plate 198 has an inner threaded surface 210 which engages the threaded surface 208. The cylindrical plate 198 also has a pair of set screws 212, 214, disposed in threaded holes 212A, 214A along an X-axis 216; and has another pair of set screws 218, 220, disposed in threaded holes 218A, 220A along a Y-axis 222.

The inner web plate 200 has a pair of set screws 224, 226, disposed in threaded holes 224A, 226A in a vertical plane through the X-axis, and has another pair of set screws 228, 230, disposed in threaded holes 228A, 230A in a vertical plane through the Y-axis 222 as shown in FIG. 3. FIG. 11 shows a top view of the cylindrical plate 198 and of the relative locations of threaded holes 212A, 214A, 218A, 220A, 224A, 226A, 228A, and 230A. A typical gap 232, which is at each of the screws 212, 214, 218, 220, separates the bearing surface 206 from an inner surface of the cylindrical plate 198. By adjusting or turning the screws 212, 214, 218, 220, cylindrical plate 198 and the tilt plate 202 can be moved in the plane of axes 216, 222 relative to the flange plate 194. By adjusting or turning the screws 224, 226, 228, 230, the tilt plate 202 and the coupler cylinder 156 can be positioned about a tilt center point 234. The point 234 is the center of concave spherical surface 236 and is the center of convex spherical surface 238 on tilt plate 202. The tilt plate 202 has a threaded surface 240 which engages a threaded surface 242 on the cylinder 156. The tilt plate 202 moves through a tilt angle 244 at a particular orientation during adjustment. The tilt angle 244 has a 360 degree orientation range or orbit. Another typical gap 246, which is disposed next to each of the screws 224, 226, 228, 230, separates a surface of the web 202 from a top surface of the tilt plate 202.

As shown in FIGS. 4, 14 and 15, the surface 242 of the cylinder 156 is threaded over the threaded surface 240. The lower inner surface 162 is threaded over a threaded surface 248 of the end coupler portion 164.

As shown in FIG. 15, the lower flanged wall 168 has a corresponding hole in the flanged upper portion 174.

As shown in FIG. 16, the lower flanged wall 168 of end coupler portion 164 has a dowel pin 250 for inserting into a corresponding orientation hole in the adjoining end face of the laparoscope (not shown).

As shown in FIG. 17, the ring member 172 has an inner threaded surface 252, which is threaded over a threaded surface on the flanged upper portions 174.

The advantage of the laser laparoscope assembly 110 are as follows.

A) The presence of the contact point 90 and the reflected beam 92 in the prior art assembly 10 is prevented.

B) The adjusting screws 212, 214, 218, 220 permit adjustments in the plane of X-axis 216 and Y-axis 222, for aligning the beam axis 124 and the passage axis 182 at the point 234.

C) The adjusting screws 224, 226, 228, 230 permit angular adjustments about the tilt center point 234 for aligning the beam area 124 and the passage area 182 along their lengths.

D) There is substantially no loss of beam power as there is no beam interference at the entry to the laparoscope 120 adjacent to flanged portion 174, because the laser outside diameter is about 4 millimeters at the entry and the laparoscope passage surface 180 inside diameter is also about 4 millimeters at the entry.

E. Thermal damage around treated tissue is minimized and carbon deposit on treated tissue is minimized because the pulses delivered per time interval are minimized and the power setting is reduced using the assembly 110 as compared to the prior art assembly 10.

While the invention has been described in its preferred embodiment, it is to be understood that the words which have been used are words of description rather than limitation and that changes may be made within the purview of the appended claims without departing from the true scope and spirit of the invention in its broader aspects.

The embodiments of an invention in which an exclusive property or right is claimed are defined as follows:

1. A laser laparoscope assembly comprising in combination:

a laser having a laser beam passage for a laser beam having a laser beam axis;

a laparoscope having a laparoscope passage having a passage axis; and an adjustable coupler for connecting the laser to the laparoscope and for aligning the laparoscope passage axis with the laser beam axis;

said adjustable coupler comprising:

a first coupler portion fixedly connected to the laser;

a second coupler portion adjustably connected to the first coupler portion; and a third coupler portion fixedly connected to the laparoscope and adjustably connected to the second coupler portion;

said second coupler portion having offset adjusting means for moving the second coupler portion and the third coupler portion in a direction normal to the laser beam axis, thereby causing the laparoscope passage axis to intersect the laser beam axis at a center point of tilt; and said third coupler portion having tilt adjusting means for angularly displacing the third coupler portion about the center point of tilt, thereby causing the laparoscope passage axis to longitudinally align with the laser beam axis; and wherein the offset adjusting means and the tilt adjusting means each include four adjustable set screws spaced apart at substantially equal angles.

2. A laser laparoscope assembly comprising in combination:

a laser having a laser beam passage for a laser beam having a laser beam axis;

a laparoscope having a laparoscope passage having a passage axis; and an adjustable coupler for connecting the laser to the laparoscope and for aligning the laparoscope passage axis with the laser beam axis;

said adjustable coupler comprising:

a first coupler portion fixedly connected to the laser;

a second coupler portion adjustably connected to the first coupler portion; and a third coupler portion fixedly connected to the laparoscope and adjustably connected to the second coupler portion;

said second coupler portion having offset adjusting means for moving the second coupler portion and the third coupler portion in a direction normal to the laser beam axis, thereby causing the laparoscope passage axis to intersect the laser beam axis at a center point of tilt; and said third coupler portion having tilt adjusting means for angularly displacing the third coupler portion about the center point of tilt, thereby causing the laparoscope passage axis to longitudinally align with the laser beam axis; and wherein the adjustable coupler also comprises:

a coupler cylinder having an upper wall attached to the third coupler portion and having a lower wall;

an end coupler portion having an upper wall attached to the coupler cylinder lower wall and having a lower wall joined to the laparoscope;

said coupler cylinder and end coupler portion having a selected overall length to suit a tapered laser beam; and said end coupler portion having, near an entry to the laparoscope, a selected inner diameter dimension, said inner diameter dimension being approximately equal to the inner diameter dimension of the laparoscope passage.

3. The assembly of claim 2, wherein the end coupler portion has a dowel pin for inserting in a hole in an adjoining end face of the laparoscope for orientation thereof.

4. A laser laparoscope assembly comprising in combination:

a laser having a laser beam passage for a laser beam having a laser beam axis;

a laparoscope having a laparoscope passage having a passage axis; and an adjustable coupler for connecting the laser to the laparoscope and for aligning the laparoscope passage axis with the laser beam axis;

said adjustable coupler comprising:

a first coupler portion fixedly connected to the laser;

a second coupler portion adjustably connected to the first coupler portion; and a third coupler portion fixedly connected to the laparoscope and adjustably connected to the second coupler portion;

said second coupler portion having offset adjusting means for moving the second coupler portion and the third coupler portion in a direction normal to the laser beam axis, thereby causing the laparoscope passage axis to intersect the laser beam axis at a center point of tilt; and said third coupler portion having tilt adjusting means for angularly displacing the third coupler portion about the center point of tilt, thereby causing the laparoscope passage axis to longitudinally align with the laser beam axis; and wherein the first coupler portion has a flange plate fixedly connected to a lens unit which is fixedly connected to the laser;

the second coupler portion has a cylindrical plate with a plurality of adjustable, offset screws engaging the flange plate and has a lock plate overlapping the flange plate and has an inner web plate, and the third coupler portion has a tilt plate with a plurality of adjustable, tilt screws engaging the inner web plate.

* * * * *